(12) United States Patent
Ameri (10) Patent No.: US 8,731,685 B2
(45) Date of Patent: May 20, 2014

(54) IMPLANTABLE LEAD HAVING A VARIABLE COIL CONDUCTOR PITCH

(75) Inventor: Masoud Ameri, Maple Plain, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 638 days.

(21) Appl. No.: 12/328,490

(22) Filed: Dec. 4, 2008

(65) Prior Publication Data
US 2009/0149933 A1 Jun. 11, 2009

Related U.S. Application Data

(60) Provisional application No. 60/992,897, filed on Dec. 6, 2007.

(51) Int. Cl.
*A61N 1/00* (2006.01)

(52) U.S. Cl.
USPC ............ 607/116; 607/119; 607/121; 607/122

(58) Field of Classification Search
USPC ......................................... 607/119, 121, 122
See application file for complete search history.

(56) References Cited

U.S. PATENT DOCUMENTS

| | | | |
|---|---|---|---|
| 3,614,692 A | 10/1971 | Rozelle et al. |
| 4,131,759 A | 12/1978 | Felkel |
| 4,135,518 A | 1/1979 | Dutcher |
| 4,404,125 A | 9/1983 | Abolins et al. |
| 4,484,586 A | 11/1984 | McMickle et al. |
| 4,493,329 A | 1/1985 | Crawford et al. |
| 4,643,202 A | 2/1987 | Roche |
| 4,869,970 A | 9/1989 | Gulla et al. |
| 5,056,516 A | 10/1991 | Spehr |
| 5,217,010 A | 6/1993 | Tsitlik et al. |
| 5,222,506 A | 6/1993 | Patrick et al. |

(Continued)

FOREIGN PATENT DOCUMENTS

| | | |
|---|---|---|
| CN | 1762510 A | 4/2006 |
| CN | 101039619 A | 9/2007 |

(Continued)

OTHER PUBLICATIONS

Robert W. Gray, et al., Simple design changes to wires to substantially reduce MRI-induced heating at 1.5T: implications for implanted leads, Magnetic Resonance Imaging, vol. 23, Oct. 8, 2005, pp. 887-891.

(Continued)

*Primary Examiner* — Michael Kahelin
*Assistant Examiner* — Mallika D Fairchild
(74) *Attorney, Agent, or Firm* — Faegre Baker Daniels LLP (57) ABSTRACT

Systems and methods for shielding implantable leads from magnetic fields during medical procedures such as magnetic resonance imaging (MRI) are described. In various embodiments, the lead includes an inner conductor that is helically shaped and radially surrounded, at least in part, by one or more outer shielding conductors. The pitch of the inner conductor, and in some cases also the outer conductor, can be varied (e.g., continuously or at certain points) along the length of the lead, forming a plurality of high impedance points along the length of the lead which result in the dissipation of electromagnetic energy at an interrogation frequency of a magnetic resonance imaging device (e.g., 64 MHz, 128 MHz, or the like). In some embodiments, the variance in the pitch of the inner conductor follows a sinusoidal function, a modified square-wave function, or some other repeating pattern.

10 Claims, 6 Drawing Sheets

(56) References Cited

U.S. PATENT DOCUMENTS

| | | |
|---|---|---|
| 5,231,996 A | 8/1993 | Bardy et al. |
| 5,241,957 A | 9/1993 | Camps et al. |
| 5,243,911 A | 9/1993 | Dow et al. |
| 5,330,522 A | 7/1994 | Kreyenhagen |
| 5,354,327 A | 10/1994 | Smits |
| 5,378,234 A | 1/1995 | Hammerslag et al. |
| 5,387,199 A | 2/1995 | Siman et al. |
| 5,425,755 A | 6/1995 | Doan |
| 5,456,707 A | 10/1995 | Giele |
| 5,483,022 A | 1/1996 | Mar |
| 5,522,872 A | 6/1996 | Hoff |
| 5,522,875 A | 6/1996 | Gates et al. |
| 5,554,139 A | 9/1996 | Okajima |
| 5,574,249 A | 11/1996 | Lindsay |
| 5,584,873 A | 12/1996 | Shoberg et al. |
| 5,599,576 A | 2/1997 | Opolski |
| 5,609,622 A | 3/1997 | Soukup et al. |
| 5,618,208 A | 4/1997 | Crouse et al. |
| 5,728,149 A | 3/1998 | Laske et al. |
| 5,760,341 A | 6/1998 | Laske et al. |
| 5,800,496 A * | 9/1998 | Swoyer et al. ............ 607/122 |
| 5,810,887 A | 9/1998 | Accorti, Jr. et al. |
| 5,833,715 A | 11/1998 | Vachon et al. |
| 5,935,159 A | 8/1999 | Cross, Jr. et al. |
| 5,957,966 A | 9/1999 | Schroeppel et al. |
| 5,957,970 A | 9/1999 | Shoberg et al. |
| 5,968,087 A | 10/1999 | Hess et al. |
| 6,057,031 A | 5/2000 | Breme et al. |
| 6,078,840 A | 6/2000 | Stokes |
| 6,083,216 A | 7/2000 | Fischer, Sr. |
| 6,106,522 A | 8/2000 | Fleischman et al. |
| 6,141,593 A | 10/2000 | Patag |
| 6,143,013 A | 11/2000 | Samson et al. |
| 6,178,355 B1 | 1/2001 | Williams et al. |
| 6,208,881 B1 | 3/2001 | Champeau |
| 6,249,708 B1 | 6/2001 | Nelson et al. |
| 6,256,541 B1 | 7/2001 | Heil et al. |
| 6,259,954 B1 | 7/2001 | Conger et al. |
| 6,289,250 B1 | 9/2001 | Tsuboi et al. |
| 6,295,476 B1 | 9/2001 | Schaenzer |
| 6,400,992 B1 | 6/2002 | Borgersen et al. |
| 6,434,430 B2 | 8/2002 | Borgersen et al. |
| 6,456,888 B1 | 9/2002 | Skinner et al. |
| 6,493,591 B1 | 12/2002 | Stokes |
| 6,501,991 B1 | 12/2002 | Honeck et al. |
| 6,501,994 B1 | 12/2002 | Janke et al. |
| 6,510,345 B1 | 1/2003 | Van Bentem |
| 6,516,230 B2 | 2/2003 | Williams et al. |
| 6,526,321 B1 | 2/2003 | Spehr |
| 6,564,107 B1 | 5/2003 | Bodner et al. |
| 6,671,554 B2 * | 12/2003 | Gibson et al. ............ 607/37 |
| 6,721,604 B1 | 4/2004 | Robinson et al. |
| 6,813,521 B2 | 11/2004 | Bischoff et al. |
| 6,850,803 B1 | 2/2005 | Jimenez et al. |
| 6,854,994 B2 | 2/2005 | Stein et al. |
| 6,920,361 B2 | 7/2005 | Williams |
| 6,925,334 B1 | 8/2005 | Salys |
| 6,949,929 B2 | 9/2005 | Gray et al. |
| 6,978,185 B2 | 12/2005 | Osypka |
| 6,993,373 B2 | 1/2006 | Vrijheid et al. |
| 6,999,821 B2 | 2/2006 | Jenney et al. |
| 7,013,180 B2 | 3/2006 | Villaseca et al. |
| 7,013,182 B1 | 3/2006 | Krishnan |
| 7,123,013 B2 | 10/2006 | Gray |
| 7,138,582 B2 | 11/2006 | Lessar et al. |
| 7,158,837 B2 | 1/2007 | Osypka et al. |
| 7,174,219 B2 | 2/2007 | Wahlstrand et al. |
| 7,174,220 B1 | 2/2007 | Chitre et al. |
| 7,205,768 B2 | 4/2007 | Schulz |
| 7,257,449 B2 | 8/2007 | Bodner |
| 7,363,090 B2 | 4/2008 | Halperin et al. |
| 7,378,931 B2 | 5/2008 | Odahara et al. |
| 7,388,378 B2 | 6/2008 | Gray et al. |
| 7,389,148 B1 | 6/2008 | Morgan |
| 7,453,344 B2 | 11/2008 | Maeda et al. |
| 7,571,010 B2 | 8/2009 | Zarembo et al. |
| 7,610,101 B2 | 10/2009 | Wedan et al. |
| 7,765,005 B2 | 7/2010 | Stevenson |
| 7,917,213 B2 | 3/2011 | Bulkes et al. |
| 7,986,999 B2 | 7/2011 | Wedan et al. |
| 8,103,360 B2 | 1/2012 | Foster |
| 8,170,688 B2 | 5/2012 | Wedan et al. |
| 8,244,346 B2 | 8/2012 | Foster et al. |
| 8,391,994 B2 | 3/2013 | Foster et al. |
| 8,401,671 B2 | 3/2013 | Wedan et al. |
| 2002/0072769 A1 | 6/2002 | Silvian et al. |
| 2002/0111664 A1 | 8/2002 | Bartig et al. |
| 2002/0128689 A1 | 9/2002 | Connelly et al. |
| 2002/0144720 A1 | 10/2002 | Zahorik et al. |
| 2003/0050680 A1 | 3/2003 | Gibson et al. |
| 2003/0083723 A1 | 5/2003 | Wilkinson et al. |
| 2003/0083726 A1 | 5/2003 | Zeijlemaker et al. |
| 2003/0092303 A1 | 5/2003 | Osypka |
| 2003/0093138 A1 | 5/2003 | Osypka et al. |
| 2003/0139794 A1 | 7/2003 | Jenney et al. |
| 2003/0140931 A1 | 7/2003 | Zeijlemaker et al. |
| 2003/0144705 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0014355 A1 | 1/2004 | Osypka et al. |
| 2004/0064173 A1 | 4/2004 | Hine et al. |
| 2004/0064174 A1 | 4/2004 | Belden |
| 2004/0088033 A1 | 5/2004 | Smits et al. |
| 2004/0122490 A1 | 6/2004 | Reinke et al. |
| 2004/0162600 A1 | 8/2004 | Williams |
| 2004/0193140 A1 | 9/2004 | Griffin et al. |
| 2004/0243210 A1 | 12/2004 | Morgan et al. |
| 2004/0267107 A1 | 12/2004 | Lessar et al. |
| 2005/0070972 A1 | 3/2005 | Wahlstrand et al. |
| 2005/0090886 A1 | 4/2005 | MacDonald et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0182471 A1 * | 8/2005 | Wang ........................ 607/119 |
| 2005/0222642 A1 | 10/2005 | Przbyszewski et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0246007 A1 | 11/2005 | Sommer et al. |
| 2005/0272280 A1 | 12/2005 | Osypka |
| 2005/0283167 A1 | 12/2005 | Gray |
| 2006/0009819 A1 | 1/2006 | Przbyszewski |
| 2006/0030774 A1 | 2/2006 | Gray et al. |
| 2006/0041294 A1 | 2/2006 | Gray |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0106442 A1 | 5/2006 | Richardson et al. |
| 2006/0167536 A1 | 7/2006 | Nygren et al. |
| 2006/0200218 A1 | 9/2006 | Wahlstrand |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2006/0293737 A1 | 12/2006 | Krishnan |
| 2007/0106332 A1 | 5/2007 | Denker et al. |
| 2007/0112398 A1 | 5/2007 | Stevenson et al. |
| 2007/0156205 A1 | 7/2007 | Larson et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0208383 A1 | 9/2007 | Williams |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0058902 A1 | 3/2008 | Gray et al. |
| 2008/0125754 A1 | 5/2008 | Beer et al. |
| 2008/0129435 A1 * | 6/2008 | Gray ........................ 336/184 |
| 2008/0132986 A1 | 6/2008 | Gray et al. |

(56) References Cited

U.S. PATENT DOCUMENTS

| | | |
|---|---|---|
| 2008/0243218 A1 | 10/2008 | Bottomley et al. |
| 2008/0262584 A1 | 10/2008 | Bottomley et al. |
| 2009/0099440 A1 | 4/2009 | Viohl |
| 2009/0099555 A1 | 4/2009 | Viohl et al. |
| 2009/0118610 A1 | 5/2009 | Karmarkar et al. |
| 2009/0149920 A1 | 6/2009 | Li et al. |
| 2009/0198314 A1 | 8/2009 | Foster et al. |
| 2009/0270956 A1 | 10/2009 | Vase et al. |
| 2009/0281608 A1 | 11/2009 | Foster |
| 2010/0010602 A1 | 1/2010 | Wedan et al. |
| 2010/0114277 A1 | 5/2010 | Zhao et al. |
| 2010/0174348 A1 | 7/2010 | Bulkes et al. |
| 2010/0234929 A1 | 9/2010 | Scheuermann |
| 2010/0331936 A1 | 12/2010 | Perrey et al. |
| 2011/0079423 A1 | 4/2011 | Zhao et al. |
| 2011/0087299 A1 | 4/2011 | Ameri |
| 2011/0093054 A1 | 4/2011 | Ameri et al. |
| 2011/0160817 A1 | 6/2011 | Foster et al. |
| 2011/0160818 A1 | 6/2011 | Struve |
| 2011/0160828 A1 | 6/2011 | Foster et al. |
| 2011/0160829 A1 | 6/2011 | Foster et al. |
| 2011/0208280 A1 | 8/2011 | Li et al. |
| 2011/0238146 A1 | 9/2011 | Wedan et al. |
| 2012/0016451 A1 | 1/2012 | Struve et al. |
| 2012/0022356 A1 | 1/2012 | Olsen et al. |
| 2012/0053662 A1 | 3/2012 | Foster et al. |
| 2012/0109270 A1 | 5/2012 | Foster |
| 2012/0179233 A1 | 7/2012 | Wedan et al. |
| 2012/0271394 A1 | 10/2012 | Foster et al. |

FOREIGN PATENT DOCUMENTS

| | | |
|---|---|---|
| EP | 0897997 B1 | 2/1999 |
| EP | 1594564 A1 | 11/2005 |
| JP | 2004141679 A | 5/2004 |
| JP | 2005501673 A | 1/2005 |
| JP | 2005515852 A | 6/2005 |
| JP | 2005515854 A | 6/2005 |
| WO | WO9606655 A1 | 3/1996 |
| WO | WO 03/063946 | 8/2003 |
| WO | WO 03/089045 | 10/2003 |
| WO | WO2004073791 A1 | 9/2004 |
| WO | WO 2005/030322 | 4/2005 |
| WO | WO2006105066 A2 | 3/2006 |
| WO | WO 2006/093685 | 9/2006 |
| WO | WO2006093685 A1 | 9/2006 |
| WO | WO 2006/105066 | 10/2006 |
| WO | WO 2007/047966 | 4/2007 |
| WO | WO 2007/089986 | 8/2007 |
| WO | WO 2007/118194 | 10/2007 |
| WO | WO 2006/093685 | 9/2009 |
| WO | WO2010078552 A1 | 7/2010 |

OTHER PUBLICATIONS

Invitation to Pay Additional Fees and, Where Applicable, Protest Fee dated Aug. 17, 2009 from PCT Application No. PCT/US2008/085533.
International Search Report and Written Opinion of the International Searching Authority, PCT/US2008/085518, Oct. 29, 2009.
International Search Report and Written Opinion issued in PCT/US2010/024062, mailed Sep. 27, 2010.
Invitation to Pay Additional Fees and Partial Search Report, issued in PCT/US2010/024062, mailed May 7, 2010.
International Search Report and Written Opinion issued in PCT/US2009/038629, mailed Jun. 29, 2009, 11 pages.
International Search Report and Written Opinion issued in PCT/US2009/032838, mailed May 4, 2009, 14 pages.
International Search Report and Written Opinion issued in PCT/US2010/055130, mailed Mar. 10, 2011, 11 pages.
International Search Report and Written Opinion issued in PCT/US2010/055653, mailed Feb. 1, 2011, 14 pages.
International Search Report and Written Opinion issued in PCT/US2012/055673, mailed Dec. 13, 2012, 10 pages.
International Search Report and Written Opinion issued in PCT/US2010/033686 on Aug. 10, 2010, 12 pages.

* cited by examiner

IMPLANTABLE LEAD HAVING A VARIABLE COIL CONDUCTOR PITCH

CROSS-REFERENCE TO RELATED APPLICATION

This application claims the benefit of U.S. Provisional Application No. 60/992,897, filed on Dec. 6, 2007, which is hereby incorporated by reference in its entirety for all purposes.

TECHNICAL FIELD

Various embodiments of the present invention generally relate to medical devices and the simultaneous delivery of diagnostic and therapeutic treatments. More specifically, embodiments of present invention relate to medical devices and methods of shielding implantable leads from magnetic fields during medical procedures such as magnetic resonance imaging (MRI).

BACKGROUND

Magnetic resonance imaging (MRI) is a non-invasive imaging method that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage in the lead.

SUMMARY

Systems and methods are described for shielding implantable leads from magnetic fields during medical procedures such as magnetic resonance imaging (MRI). Some embodiments generally relate to a medical device, comprising a lead having a proximal section, a distal section, and a length. In some cases, the proximal section can be coupled to a pulse generator (e.g., a pacemaker, a cardiac defibrillator, monitoring devices such as sensors, and/or the like), the distal section can include an electrode and can be implanted within a heart of a patient. In this configuration, for example, the lead is configured to convey electrical signals between the heart and the pulse generator through an inner conductor.

The lead includes, in various embodiments, an inner conductor that is helically shaped. In some embodiments, the inner conductor may be radially surrounded, at least in part, by one or more outer shielding conductors. The pitch of the inner conductor can continuously vary along the length of the lead forming a plurality of high impedance points along the length of the lead to inhibit the absorbed electromagnetic energy from traveling along the length of the lead at an interrogation frequency of a magnetic resonance imaging device (e.g., 64 MHz, 128 MHz, or the like). For example, in one or more embodiments, the variance in the pitch of the inner conductor follows a sinusoidal function, a modified square-wave function, a triangle function, a saw-tooth function, a quadratic function, or some other repeating pattern. In some embodiments, the one or more outer shielding conductors can have a pitch that varies continuously along the length of the lead (e.g., via a sinusoidal function, a modified square-wave function, or some other repeating pattern), or alternatively has a pitch that changes at one or more points along the length of the lead.

In various embodiments, the lead can include a low impedance insulation near the proximal section and the distal section of the lead. During an MRI procedure, the low impedance insulation can cause the electromagnetic energy produced by the MRI device to be dissipated along the body tissue adjacent to the length of the lead to reduce energy transfer of the electromagnetic energy to the electrode.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
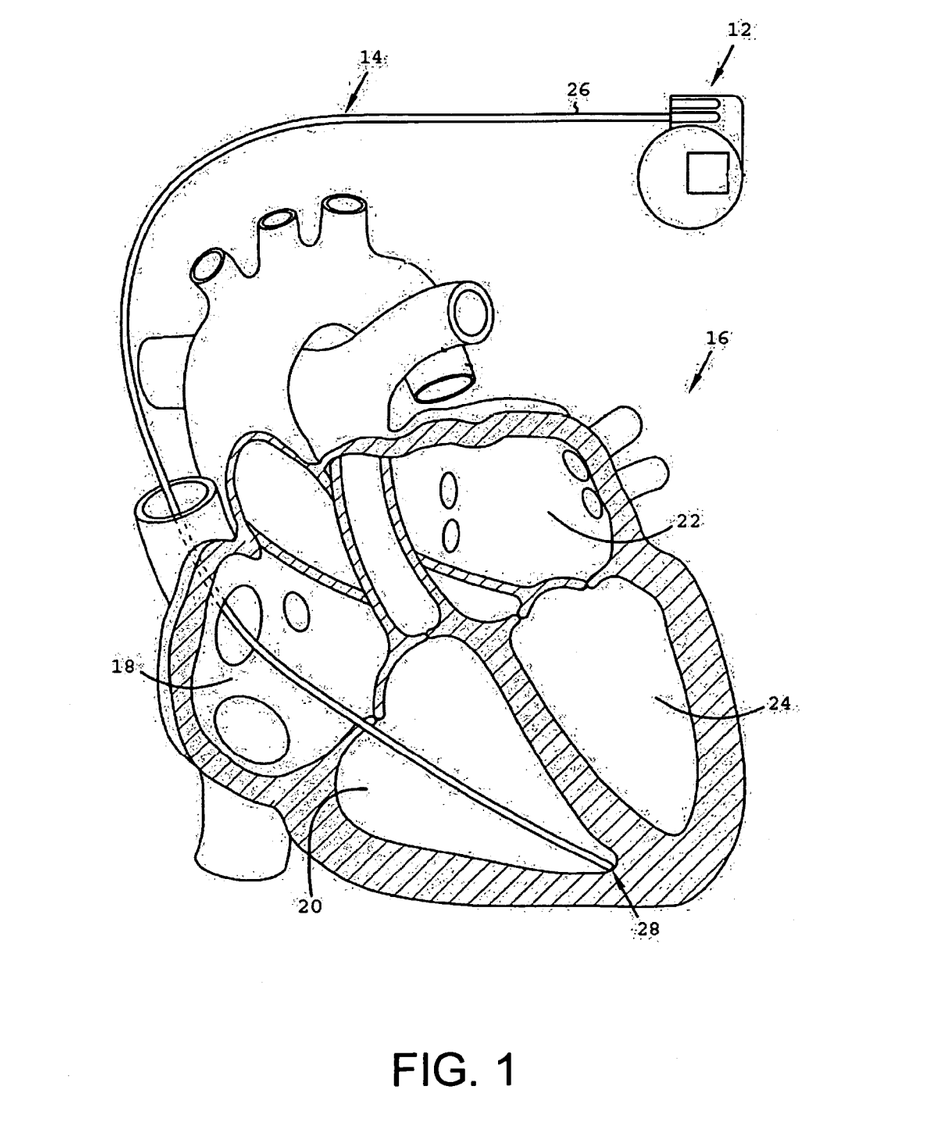
FIG. 1 is a schematic view of an illustrative medical device having a lead implanted within the body of a patient.

FIG. 1 is a schematic view of an illustrative medical device 12 equipped with a lead implanted within the body of a patient. In the illustrative embodiment depicted, the medical device 12 comprises a pulse generator implanted within the body. The medical device can be coupled to a lead 14 deployed in the patient's heart 16. The heart 16 includes a right atrium 18, a right ventricle 20, a left atrium 22, and a left ventricle 24. The pulse generator 12 can be implanted subcutaneously within the body, typically at a location such as in the patient's chest or abdomen, although other implantation locations are possible.

A proximal portion 26 of the lead 14 can be coupled to or formed integrally with the pulse generator 12. A distal portion 28 of the lead 14, in turn, can be implanted within a desired location within the heart 16 such as the right ventricle 20, as shown. Although the illustrative embodiment depicts only a single lead 14 inserted into the patient's heart 16, it should be understood, however, that multiple leads can be utilized so as to electrically stimulate other areas of the heart 16. In some embodiments, for example, the distal portion of a second lead (not shown) may be implanted in the right atrium 18. In addition, or in lieu, another lead may be implanted at the left side of the heart 16 (e.g., in the coronary veins) to stimulate the left side of the heart 16. Other types of leads such as epicardial leads may also be utilized in addition to, or in lieu of, the lead 14 depicted in FIG. 1.

During operation, the lead 14 can be configured to convey electrical signals between the heart 16 and the pulse generator 12. For example, in those embodiments where the pulse generator 12 is a pacemaker, the lead 14 can be utilized to deliver electrical therapeutic stimulus for pacing the heart 16. In those embodiments where the pulse generator 12 is an implantable cardiac defibrillator, the lead 14 can be utilized to deliver electric shocks to the heart 16 in response to an event such as a heart attack. In some embodiments, the pulse generator 12 includes both pacing and defibrillation capabilities.

Figure 2:
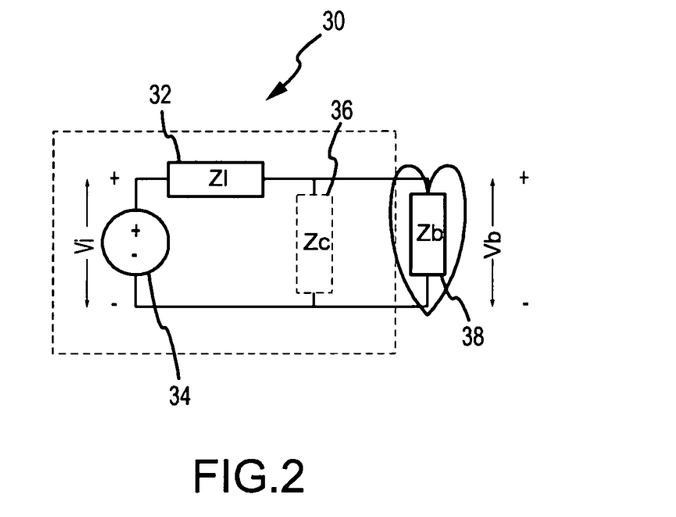
FIG. 2 is a schematic view showing a simplified equivalence circuit for the lead of FIG. 1.

FIG. 2 is a schematic view showing a simplified equivalence circuit 30 for the lead 14 representing the RF energy picked up at the lead 14 resulting from electromagnetic energy produced by an MRI scanner. During imaging, the length L of the lead 14 functions similar to an antenna, receiving the RF electromagnetic energy that is transmitted into the body from the MRI scanner. Voltage source 34 in FIG. 2 represents the resultant voltage received by (or picked up by) the lead 14 from the RF electromagnetic energy produced by the MRI scanner. The RF energy picked-up by the lead 14 may result, for example, from the magnetic field produced during magnetic resonance imaging or from RF interference from another device location inside or outside of the patient's body.

The Zl parameter 32 in the equivalence circuit 30 represents the equivalent impedance exhibited by the lead 14 at the RF frequency in the MRI scanner. The impedance value Zl 32 may represent, for example, the parallel inductance and capacitance components exhibited by the lead 14 at an RF frequency of 64 MHz for a 1.5 T MRI scanner or 128 MHZ for a 3.0 T MRI scanner. The magnetic field strength of an MRI scanner typically ranges from 0.2-3 Tesla. Accordingly, the range of the RF frequency would be between 8.53 to 128 MHz. However, there are other MRI scanners that operate at other magnetic field strengths, such as, but not limited to, 5, 7, 9, or even 12 Tesla. The MRI frequency would be equal to approximately 42.58 MHz per Tesla.

Zb 38 may represent the impedance of tissue at the point of lead contact. Zc 36, in turn, may represent the capacitive coupling of lead to surrounding tissue along the length of the lead, which is a path for the high frequency current (energy) to leak into the surrounding tissue at the RF frequency of the MRI scanner. Minimizing the (absorbed) energy (represented by source Vi 34) reduces the energy that will get transferred to the tissue at the point of lead contact to tissue.

The circuit representation in FIG. 2 and the associated equation described below are for the purpose of illustrating the concept of lead heating in an MRI environment. At frequencies where the wavelength of voltage (current) is close to the size of circuit, a simple lumped sum system (like the circuit illustrated in FIG. 2) may not accurately model the behavior of the lead in the MRI environment. Consequently, in those circumstances where a lumped system does not accurately model the behavior, a distributed system should be used along with Maxwell's equation for a proper mathematical description of the circuit. A distributed model is a model of a system where the circuit components (e.g., resistors, inductors, capacitors, etc) are distributed across the circuit geometries. In distributed circuits, the voltage at a node (in this case the lead) is not constant and is represented by a wave. In some cases, the approximating distributed model can be created by cascading lumped element equivalent components of small sections of the circuit.

As can be further seen in FIG. 2, the lead 14 has some amount of leakage 36 into the surrounding tissue at the RF frequency. As further indicated by 38, there is also an impedance at the point of contact (e.g., within heart 16) of the lead electrode to the surrounding body tissue. The resulting voltage Vb delivered to the body tissue is related by the following formula:

$Vb = Vi\, Zbe/(Zbe + Zl)$, where $Zbe = Zb$ in parallel with $Zc$.

The temperature at the tip of the lead 14 where contact is typically made in the surrounding tissue is related to the power dissipated at 38 (i.e., at "Zb"), which, in turn, is related to the square of Vb. To minimize temperature rises resulting from the power dissipated at 38, it is thus desirable to minimize Vi (34) and Zc (38) while also maximizing Zl (32). In some embodiments, the impedance Zl (32) of the lead 14 can be increased at the RF frequency of the MRI scanner, which aids in reducing the power dissipating into the surrounding body tissue at 38.

In some embodiments, the impedance of the lead 14 can be increased by adding impedance to the lead and/or by a suitable construction technique. For example, the impedance of the lead 14 can be increased by increasing the diameter of the conductor coil, although other configurations are possible. For a helical lead construction, if the resonance frequency of the lead is above the RF frequency of the MRI, then impedance exhibited by helical coil acts as an inductor. For an inductor, increasing the cross section of the coil area increases the inductance and, as a result, increases the impedance of the lead 14.

In certain embodiments, the lead 14 can be detuned so as to prevent resonance within the lead 14. For the illustrative embodiment shown in FIG. 1, for example, the lead 14 functions as an antenna having a resonance frequency at length L=integer×λ/2. In some embodiments, the length of the lead 14 can be chosen so as to avoid resonance within the lead 14. In various embodiments, the length of the lead 14 can be between 40 cm and 100 cm.

However, leads can be designed in such a way that is not uniform. Variation in construction of a lead can result in variations of the characteristic impedance of the lead along the length. For example, in some embodiments, the variation could be the pitch of the coil used in lead construction. One benefit of having a variable pitch coil design in accordance with some embodiments is that the variable pitch coil provides robustness in providing high impedance points along the length of the lead with respect to lead stretching and compression. Stretching and compression of the lead can be caused, for example, by manufacturing tolerances, handling, usage (e.g., pulling, bending, etc), as well as other factors.

Based on the theory of transmission lines, mismatch in the characteristic impedance can result in reflections of electromagnetic waves. The incident and reflected waves (from the mismatch impedance points) adds vectorially. Consequently, some embodiments adjust the pattern repetition distance to be less than a quarter wavelength if the pattern of lead construction is repeated. At quarter wave length segments, the incident and reflected waves are 180 degrees out of phase and therefore subtract from each other reducing the magnitude of the electromagnetic waves. According to various embodiments, the quarter wave length can be in the range of 10 cm to 25 cm.

In some embodiments, shielding can be added to the lead 14 to reduce the amount of electromagnetic energy picked-up from the lead 14. For example, the energy picked up from the shielding can be coupled to the patient's body along the length L of the lead 14, preventing it from coupling to the lead tip.

Figure 3:
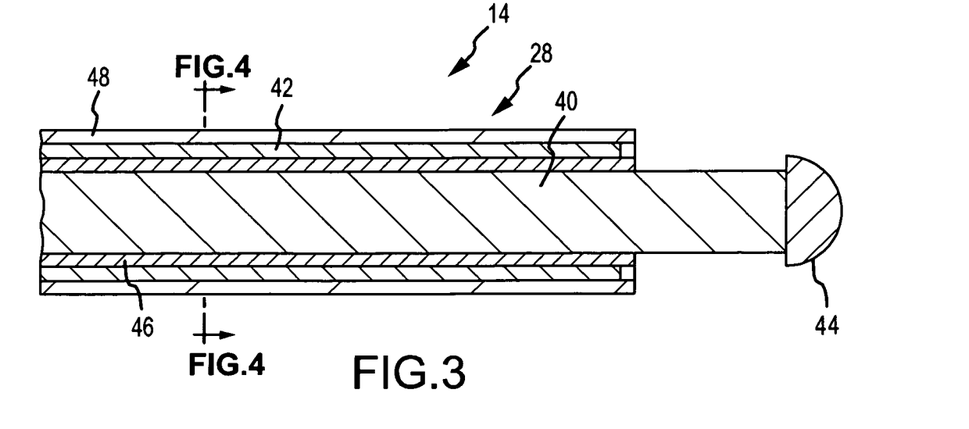
FIG. 3 is a longitudinal cross-sectional view showing the distal portion of an uncoiled lead in accordance with an illustrative embodiment.

FIG. 3 is a schematic view showing the distal portion 28 of the uncoiled lead 14 of FIG. 1 in greater detail. FIG. 3 may represent, for example, a longitudinal cross-sectional view of the lead 14 prior to being subjected to a winding step to impart the helical shape to the lead 14, as discussed further herein. In some embodiments, and as shown in FIG. 3, the lead 14 includes an inner conductor 40 having a proximal end (not shown) and a distal end. The distal end of the conductor can be configured to contact the surrounding tissue (e.g., through electrode 44) to provide therapeutic energy to a desired treatment site such as the patient's heart.

Figure 4:
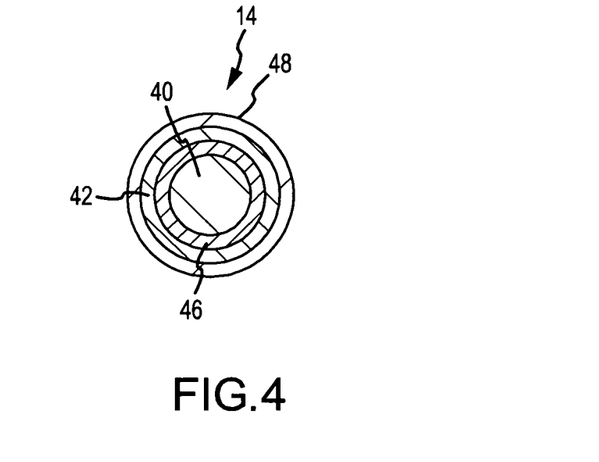
FIG. 4 is a transverse cross-sectional view of the lead of FIG. 3.

In some embodiments, and as further shown in conjunction with a transverse cross-sectional view of the lead in FIG. 4, the lead 14 further includes an outer shield 42 that extends along all or a portion of the length of the lead 14, and is configured to at least in part radially surround the inner conductor 40 to prevent RF electromagnetic waves generated by an MRI scanner from interfering with the electrical signals delivered through the lead 14. Although only a single outer shielding conductor 42 is shown in the embodiment of FIGS. 3-4, multiple outer shields may be provided in other embodiments. Similarly, other embodiments include multiple leads with one or more outer shielding conductors 42.

The lead 14 further includes a number of layers of insulating material disposed about the outer shielding conductor 42 and the inner conductor 40. A first layer 46 of insulating material, for example, may insulate the inner conductor 40 from the outer shielding conductor 42. A second layer 48 of insulating material, in turn, may insulate the outer shielding conductor 42 from the body tissue surrounding the lead 14. Some embodiments use thinner insulation with the highest dielectric material that can be used in implants. Some embodiments can use a low impedance insulation made from a material with a relative dielectric constant of five to ten times the dielectric constant of the inner conductor.

Figure 5:
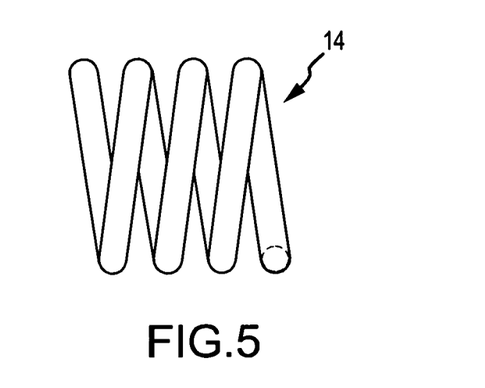
FIG. 5 is a view showing the lead of FIGS. 3-4 having a helix configuration.

The shield by itself typically exhibits high impedance along the length of the lead compared to a low impedance along a cross-section of the lead. This high impedance can be achieved, for example, by inductance from coiling the lead wire. FIG. 5 is a view showing the illustrative uncoiled lead 14 of FIGS. 3-4 having a helix configuration along its length. If the turns of the lead 14 as shown in FIG. 5, and consequently, turns of the outer shielding conductor 42, touch the adjacent ones, a short circuit is created and the effect of inductance is eliminated. In some embodiments, second insulating layer 48 can prevent the turns of the coil shield from coming in contact with each other when uncoiled lead 14 of FIGS. 3-4 is placed in a helix configuration as shown in FIG. 5. In some embodiments, the highest pitch for a given diameter of the lead that can produce a coil that has an acceptable mechanical characteristic that is desirable.

Another reason for having insulation 48 in some embodiments is to control the "turn by turn capacitance" of the lead. If fluid, such as blood, penetrates inside the lead, an increase in the capacitance between coil winding turns can result. The relative dielectric constant of water or blood is about 80 compared to 1 for air. Since capacitance is proportional to relative dielectric constant, this results in a significant shift in resonance frequency.

Figure 7:
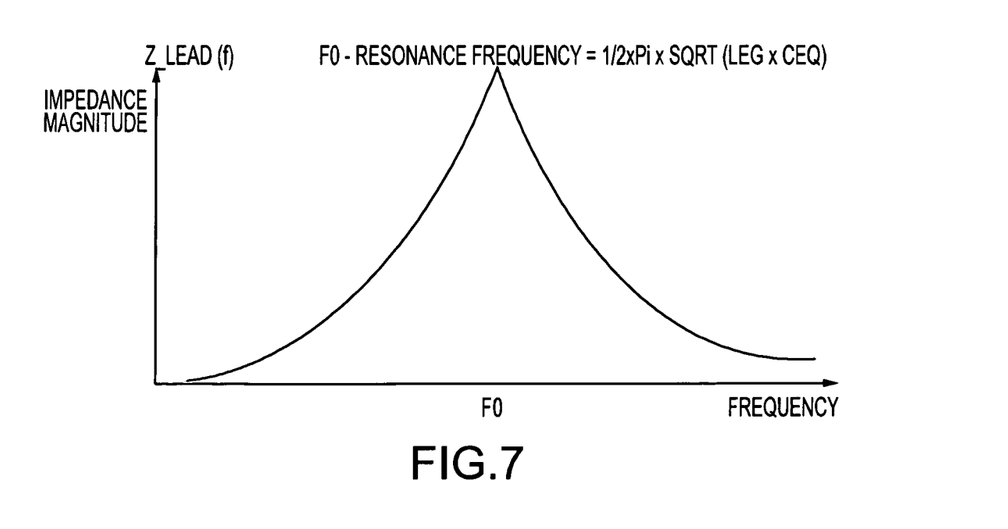
FIG. 7 is a graph showing the impedance magnitude of the lead versus RF frequency in an MRI environment.

For example assume that the resonance frequency of the lead is about 100 MHz. In this case, the inductance of the lead would be dominant since the frequency of the RF waveform is 64 MHz for 1.5 T MRI. If blood penetrates between winding turns, a shift in the resonance frequency of the lead from about 100 MHz to about 11 MHz would result. This resonance frequency is now lower than the operating frequency of the MRI (64 MHz), in which case the turn by turn capacitance is dominant. In this case, RF energy instead of traveling through inductance created by coil windings, travels through the turn by turn capacitance and lead impedance is reduced. Note that the further the operating frequency is from the resonance frequency, the lower the impedance of the lead (see, e.g., FIG. 7).

In some embodiments, lead 14 can have a low impedance path to surrounding tissue at or near the electrode 44, but a high impedance (e.g., trace impedance) along the length of the lead. For example, in the embodiments shown in FIG. 3, a lower impedance at or near the electrode 44 can be created by terminating the outer conductor 42 and/or any insulating material before the electrode 44. More specifically, FIG. 3 shows the wire integrated with the shielding.

According to some embodiments, a thin insulation can be used to provide a high capacitance between the electrode 44 and surrounding tissue. The thin insulation can also provide a low impedance path for MRI induced RF energy. However, the thin insulation generally does not effect the impedance for therapy delivery that typically contains energy with low frequency contents. In certain embodiments, the impedance of the inner conductor can be designed to be similar to the impedance of the one or more outer shielding conductors 42. However, in other embodiments, the impedance of the inner conductor can be different from the impedance of the one or more outer shielding conductors 42.

In various embodiments, the pitch of a helix is the width of one complete helix turn, measured along the helix axis. In accordance with various embodiments, the inner conductor 40 can have an average pitch between, and including, five mils (i.e., 5/1000 of inch) and fifty mils (i.e., 50/1000 of inch). In some embodiments, inner conductor 40 may have a maximum pitch of approximately five mils, while in other embodiments the maximum pitch may be more or less. The variation of the pitch in various embodiments can also be a function of wire diameter. For example, if the wire diameter is 3 mils, then the minimum pitch can be slightly larger than 3 mils. If the wire lead is insulated and turn by turn capacitance is not large, then the minimum pitch can be 3 mils in some embodiments.

Figure 6:
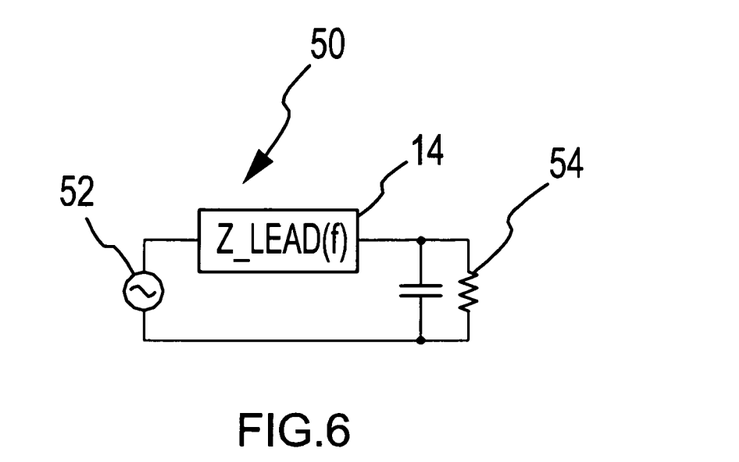
FIG. 6 is a schematic view showing an equivalence circuit for the lead of FIG. 5.

FIG. 6 is a schematic view showing an equivalence circuit 50 for the coiled helix-shape lead 14 of FIG. 5. As shown in FIG. 6, the inductance of a helix lead in conjunction with the capacitance between its winding turns forms a resonance circuit 50 along the length of the lead. The RF electromagnetic energy received during an MRI procedure produces a voltage 52. The lead 14 has an equivalent inductance and capacitance within the circuit 50, as indicated generally by "Z_lead(f)". The point of electrode contact to tissue has an equivalent impedance, as indicated by 54. The impedance "Z_lead(f)" for the lead 14 increases in magnitude at the RF frequency of the MRI scanner. This can be seen, for example, in FIG. 7, which shows a dramatic increase in the impedance magnitude at resonance frequency "F0".

Figure 8A:
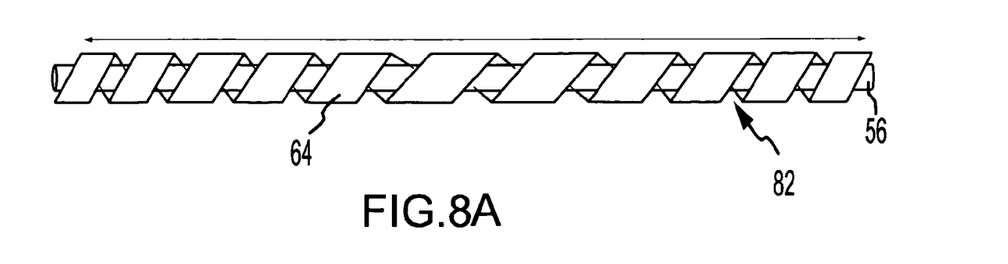
FIG. 8A is a view showing a lead having a variable coil conductor pitch.
Figure 8B:
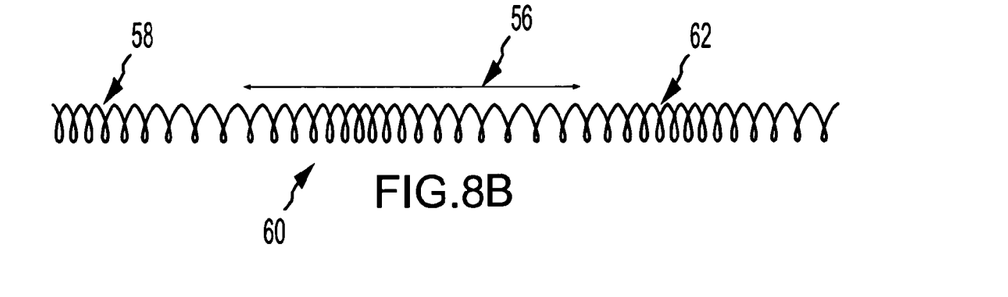
FIG. 8B shows one illustrative embodiment where high impedance frequency dependent points are created along the length of the lead.

In certain embodiments, the pitch of the lead and/or lead shielding can be varied along its length to alter the impedance characteristics of the lead and/or shielding in a desired manner. The pitch can vary continuously or at fixed points. For example, the uncoiled lead 56 in FIG. 8A can be formed in a helix-like shape with a pitch that can vary to provide one or more high impedance frequency dependent points. FIG. 8B shows one illustrative embodiment where high impedance frequency dependent points 58, 60, 62 are created along the length of the lead 56, reducing the RF pickup energy in addition to reducing the transmission of the RF pickup energy into the inner conductor. In some embodiments, an illustrative shielding 64 having a variable pitch can also be placed about the lead 56, as further shown in FIG. 8A. In other embodiments, however, the lead can include a shielding having a fixed pitch, shielding only along a portion of the lead, or a lead having no outer shielding at all.

In some embodiments, the lead pitch pattern is repeated several times along the length of the lead 56 such that the pitch pattern covers the lead length of less than ¼ of the wavelength of the highest frequency of interest. For example, for a lead 56 subjected to an RF MRI frequency of 64 MHz, the lead pitch pattern may be repeated approximately every 117 centimeters, which corresponds to a ¼ wavelength at this frequency. During an MRI scan, this detuning of the lead 56 prevents the lead 56 from approaching the antenna resonance length, thus minimizing the RF energy picked-up from the lead 56.

Figure 9:
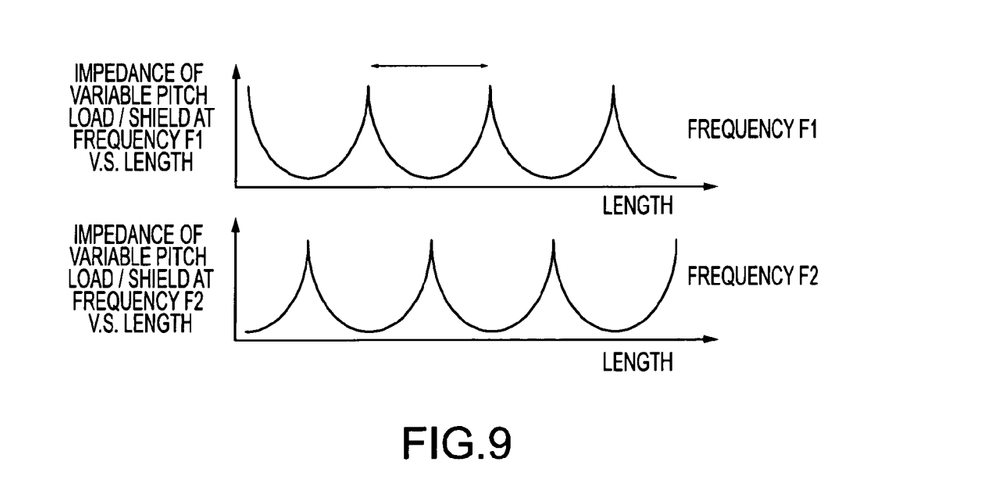
FIG. 9 shows two graphs of the impedance of a variable coil conductor pitch verses the length of the lead at two different MRI frequencies.

FIG. 9 shows two graphs of the impedance of a variable-pitch lead versus the length of the lead at two different RF frequencies, F1 and F2. As shown in FIG. 9, the locations along the length of the lead where a relatively high impedance occurs depends on the surrounding pick-up frequency F1, F2 in the environment. Thus, for frequency F1 shown in the top graph, the location along the length of the lead where an increase of impedance occurs is different than for frequency F2 shown in the bottom graph. This can be seen by a shift in the impedance peaks in the top and bottom graphs shown in FIG. 9.

Figure 10:
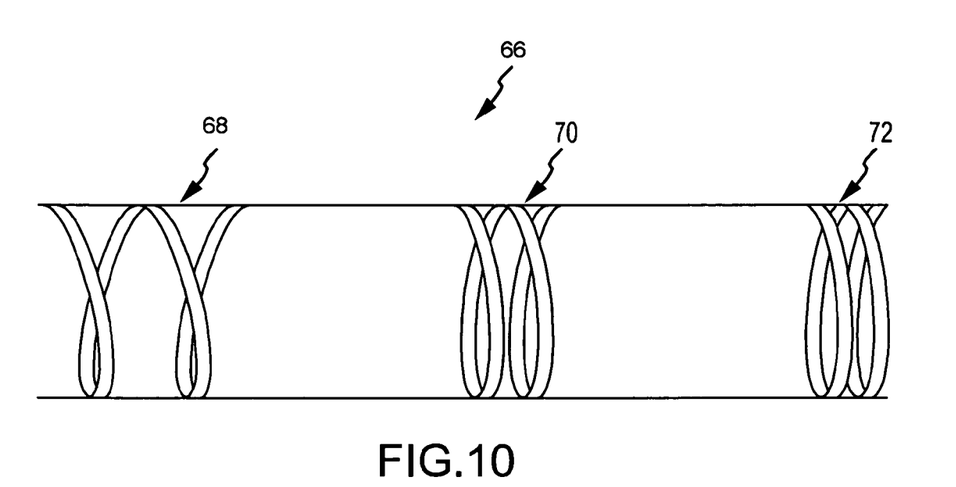
FIG. 10 is a view showing a variable pitch lead in accordance with an illustrative embodiment.
Figure 11:
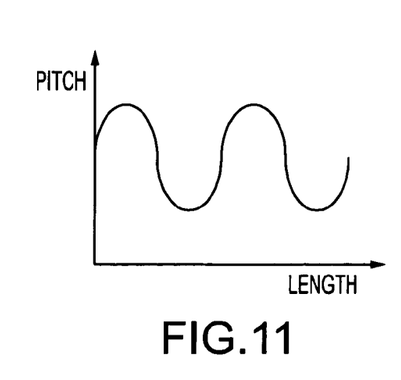
FIG. 11 is a graph showing the pitch of a lead following a sinusoidal function.
Figure 12:
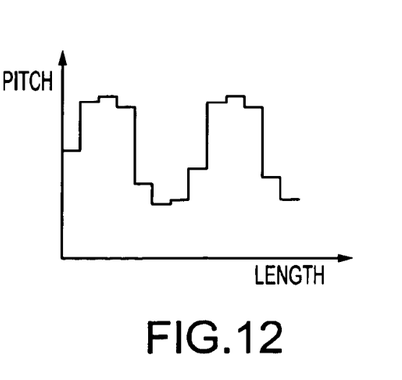
FIG. 12 is a graph showing the pitch of a lead following a modified square-wave function.

FIG. 10 is a view showing a variable pitch lead 66 in accordance with an illustrative embodiment. As shown in FIG. 10, the lead 66 may include a first section 68, a second section 70, and a third section 72. The variance of pitch along each section 68, 70, 72 may follow a particular function. As can be further seen in FIG. 11, for example, the pitch of the lead 66 may follow a function that varies sinusoidally along the length of the lead 66. The variance in pitch may follow other functions such as a square wave or other such function. In one alternative embodiment depicted in FIG. 12, for example, the pitch of lead 66 may follow a modified square-wave function. Other pitch configurations are possible, however.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An implantable medical device, comprising:
a lead having a proximal section adapted to be coupled to a pulse generator, a distal section adapted to be located within a heart of a patient, and a length, wherein the lead is configured to convey electrical signals between the heart and the pulse generator through an inner conductor;
the inner conductor having a helix-like shape with a first inner conductor pitch, the inner conductor including a plurality of high impedance elements having a second inner conductor pitch different than the first inner conductor pitch along the length of the lead such that the inner conductor includes portions having the second inner conductor pitch interspersed with portions having the first conductor pitch, wherein a distance between each of the high impedance elements is less than ¼ of a wavelength of a highest frequency of one or more magnetic resonance imaging (MRI) frequencies such that, when the lead is exposed to the one or more MRI frequencies, incident and reflected waves inducted within the inner conductor subtract from each other to detune the inner conductor at the one or more MRI frequencies; and
an outer conductor having a helix-like shape radially surrounding at least a portion of the inner conductor, wherein the outer conductor has an outer conductor pitch that varies at one or more locations along the length of the lead.

2. The implantable medical device of claim 1, wherein the outer conductor pitch continuously varies.

3. The implantable medical device of claim 1, wherein the inner conductor pitch follows a sinusoidal function or a modified square-wave function.

4. The implantable medical device of claim 1, further comprising shielding with a high impedance along the length of the lead and a low impedance along a cross-section.

5. The implantable medical device of claim 1, wherein an impedance of the inner conductor is similar to an impedance of the outer conductor.

6. The implantable medical device of claim 1, wherein the proximal section of the lead is adapted to be coupled to a pacemaker or a cardiac defibrillator.

7. The implantable medical device of claim 1, further comprising one or more layers of insulating material disposed about the outer conductor and the inner conductor.

8. A medical lead, comprising:
an inner conductor having a helix-like shape with a first inner conductor pitch, the inner conductor including a plurality of high impedance elements having a second inner conductor pitch different than the first inner conductor pitch along the length of the lead such that the inner conductor includes portions having the second inner conductor pitch interspersed with portions having the first conductor pitch, wherein a distance between each of the high impedance elements is less than ¼ of a wavelength of a highest frequency of one or more magnetic resonance imaging (MRI) frequencies such that, when the lead is exposed to the one or more MRI frequencies, incident and reflected waves inducted within the inner conductor subtract from each other to detune the inner conductor at the one or more MRI frequencies; and
an outer conductor having a helix-like shape and radially surrounding at least a portion of the inner conductor, wherein the outer conductor has an outer conductor pitch that varies at one or more locations along the length of the lead.

9. The medical lead of claim 8, wherein the outer conductor pitch continuously varies.

10. The medical lead of claim 8, wherein the high impedance elements inhibit electromagnetic energy from traveling along the length of the lead at one or more frequencies between 8.53 MHz and 128 MHz.

* * * * *